United States Patent [19]

Murphy et al.

[11] 4,184,768
[45] Jan. 22, 1980

[54] SELF-CALIBRATING PHOTOACOUSTIC APPARATUS FOR MEASURING LIGHT INTENSITY AND LIGHT ABSORPTION

[75] Inventors: John C. Murphy, Ellicott City; Leonard C. Aamodt, Silver Spring, both of Md.

[73] Assignee: The Johns Hopkins University, Baltimore, Md.

[21] Appl. No.: 848,706

[22] Filed: Nov. 4, 1977

[51] Int. Cl.$^2$ .......................... G01J 3/42; G01J 1/56
[52] U.S. Cl. .................................. 356/326; 250/252; 250/351; 356/216; 356/217
[58] Field of Search ................. 356/97, 204, 216, 217, 356/229, 234, 326, 483; 250/252, 341, 343, 351, 352

[56] References Cited

U.S. PATENT DOCUMENTS 4,051,371   9/1977   Dewey, Jr. et al. ................. 250/343

FOREIGN PATENT DOCUMENTS 241761   8/1969   U.S.S.R. ................................. 356/216

*Primary Examiner*—Vincent P. McGraw

*Attorney, Agent, or Firm*—Robert E. Archibald; Marc A. Block

[57] ABSTRACT

Pulsed light and readily measurable pulsed electrical energy are independently applied to a solid black, conductive sample in a gas-filled photoacoustic cell, each causing the black sample to heat. The heating of the black sample causes a pressure wave in the cell, which can be detected and measured. By adjusting the pulsed electrical energy, the pressure wave resulting from the pulsed electrical energy can be made to relate to the pressure wave resulting from the pulsed light in a predetermined manner. The pulsed light input intensity can then be measured in electrical units based on the measurable input of the electrical energy pulses. In this manner, the invention can be used as a radiometer. A second application for the present apparatus is in calibrating photoacoustic spectroscopy (PAS) cells. The PAS cell can be self-calibrated by discontinuing the light pulses and relating the pressure wave output to the electrical energy pulse input. The measurement then of light absorption in a test sample, which need be neither black nor conductive, can be made in absolute energy units based on the self-calibration relationship.

33 Claims, 4 Drawing Figures

SELF-CALIBRATING PHOTOACOUSTIC APPARATUS FOR MEASURING LIGHT INTENSITY AND LIGHT ABSORPTION

STATEMENT OF GOVERNMENTAL INTEREST

The invention herein described was made in the course of or under a contract or subcontract thereunder, with the Department of the Navy.

BACKGROUND OF THE INVENTION

Recently Photoacoustic Spectroscopy (PAS) has emerged as a significant new tool for the study of light absorption in solids and liquids. It is especially useful in cases where strong light scattering or opacity in the absorbing sample makes the application of conventional optical absorption methods difficult. It also has application in studying energy conversion processes which compete with thermalization in the sample for the energy in the absorbed light. At its current state of development PAS-derived information has been primarily qualitative in nature with the principal experimental result being the determination of the relative spectral amplitude of the PAS signal as a function of wavelength. Detailed considerations of the responsivity of fluid filled photoacoustic cells have shown that the measured PAS signal depends on thermal diffusion in four regions which constitute the complete cell, viz. the light-absorbing sample, the support or backing which holds the sample, the gas or liquid pressure transducing medium, and the cell walls and light-admitting window. In keeping with the diffusion character of the basic processes responsible for generation of the effect, the PAS signal is scale dependent, that is, it depends on the size of each region of the photoacoustic cell relative to the thermal diffusion lengths, $\mu_i = [2a_i/\omega]^{\frac{1}{2}}$, in each region, where a is the thermal diffusivity, and $\omega$ the angular modulation frequency. The thermal diffusion lengths in both the cell and sample depend on the modulation frequency and hence the cell responsivity is frequency dependent. Since the basic objective of the measurement is the determination of the sample properties, including the optical absorption co-efficient, these cell-dependent effects are experimental impediments which must be removed if the sample properties are to be determined. Fortunately, for fixed modulation frequency operation in a single cell, these complications do not interfere with the measurement of the relative sample absorption spectrum. This type of measurement has characterized the bulk of prior art PAS measurement methods.

U.S. Pat. Nos. 3,911,276; 3,893,771; 3,820,901; and 3,700,890 all describe photoacoustic spectrometers which measure relative absorption spectra without reference to absolute values of energy. The problems of cell structure dependency and the inability to translate data between cells remain unsolved by the prior art techniques. Another U.S. Pat. No. 3,948,345 employs a metal black sample in a standard cell wherein pulsed light is split between the standard cell and a test cell including a test sample. A comparison between the pressure waves generated in the standard cell and the pressure waves generated in the test cell is made to determine the relative absorption in the test cell. The reference does not provide an absolute measurement independent of cell characteristics. The conductivity of the black sample is not important in the reference; the black sample is not used for self-calibration.

SUMMARY OF THE INVENTION

The present invention is basically a marriage between two conventional measuring techniques which together provide new and unexpected useful results. The concept of photoacoustics is a well-known one, wherein a pulsed light beam directed towards a sample heats the sample which in turn generates pressure waves which can be measured. Similarly, the theory of Joule-heating a wire to heat a sample, thereby increasing the temperature of the sample and producing pressure waves in the surrounding gas is also known. The present invention, by switching between the photoacoustic effect and the Joule effect, can measure, on an absolute scale, the intensity of light striking the sample and can be used in calibrating a standard photoacoustic spectrometer cell in terms of absolute conventional energy units.

The ramifications of coupling the two techniques by means of a metal black conductive film are significant. First, as suggested by the previous discussion, the present invention can be used as a radiometer which measures light intensity in terms of the electric power in. Such a radiometer is not only self-calibrating but is also independent of the wavelength and pulse frequency of the incoming light. Second, as a photoacoustic spectrometer, the invention can be used to make standard measurements that are independent of cell characteristics. There are numerous applications which require cell measurements made at various pulse frequencies of light. While the prior art devices could not be adapted for use at differing frequencies, the present invention features such flexibility. Third, the present apparatus retains the advantages of the prior art PAS devices. These include the non-destructive measurement of light absorption in solids and liquids where strong light scattering and opacity in the absorption techniques difficult.

A number of applications, such as the calibration of microphones, the detection of pollutants, the detection of bacteria, the analysis of blood, the measuring of uniformity of coatings on floor tile and the like, and examining chromotographic films for impurities may use PAS techniques which employ the present invention.

It is thus an object of the present invention to provide a useful improvement for prior art spectrometers, which adds the capability of measuring the light absorption of a sample in absolute, conventional, energy units.

It is another object of the invention to provide a self-calibrated radiometer based on the photoacoustic effect.

It is still another object of the invention to provide a photoacoustic spectrometer the cell of which is calibrated and, which based on the calibration, measures light absorption in a sample in absolute energy units.

It is yet another object of the invention to combine a photoacoustic cell with a thermophone cell to produce a self-calibrating cell.

It is still another object of the invention to provide a useful heat absorbing element that uses an electrically conductive, spectrally flat, black sample to permit heat absorption from optical and electrical inputs.

DESCRIPTION OF THE INVENTION

Figure 1:
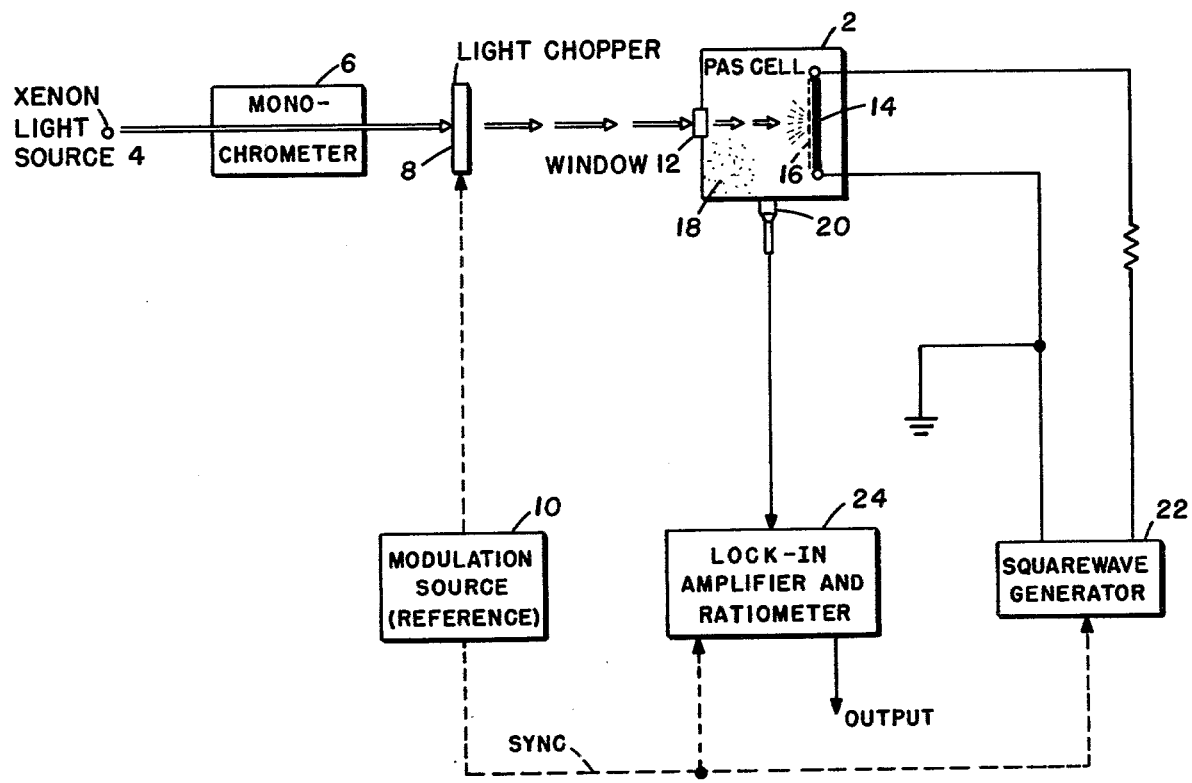
FIG. 1 is a block diagram of a photoacoustic spectrometer (PAS) showing optical and electrical heating of a metal black sample.

Referring to FIG. 1, apparatus is illustrated which measures the intensity of light entering a photoacoustic cell 2 in terms of absolute, quantitative, accurate, and conventional electrical units. Light from a xenon light source 4, which might also be a laser or other light source, passes through a monochrometer 6 which confines the light in spectral frequency and a conventional light chopper 8 which produces light pulses (shown as arrows in series) at a frequency regulated by a modulation source 10. The light pulses enter cell 2 through a window 12 and impinge on a solid black, optically absorbing, electrically conductive sample 14. Several members of the carbon black/pyrolitic graphite family satisfy these requirements. Preferably, a metal black electrolytically-plated on a chromium layer, which is vacuum deposited on a glass substrate, can be used. The light pulses are absorbed by the spectrally flat black sample 14 which experiences a rise in temperature. The rise in temperature in the black sample 14 induces a temperature rise and related pressure variations in the fluid, including liquid or gas, boundary layer 16 adjacent to the black sample 14. The pressure changes are transmitted through the cell as a series of pulses or waves or similar disturbances in fluid 18, enclosed within cell 2. A microphone 20 is provided to convert the pressure waves (which include the pulses and other such acoustic or other longitudinal disturbances) into electrical signals. Instead of the microphone 20, a thermometer or gas diffusion measuring device may be substituted to measure temperature or transport variations rather than pressure; however, with a loss of accuracy.

In addition to the light input, a second energy source is provided in cell 2 which makes cell 2 not only a photoacoustic cell but also a thermophone cell. That is, the electrically conductive black sample 14 is Joule-heated to create further temperature and pressure changes in cell 2. Specifically, a squarewave generator 22 provides current through the electrically conductive black sample 14 generating heat and resultant pressure waves which can be detected and measured by microphone 20. The signals detected by microphone 20 for the two cases of optical and electrical heating are equal when the same total energy is deposited by each. This equality is used in the present disclosure as the basis of the applications cited. For example, if the current pulse from squarewave generator 22 is caused to occur when the light pulse is not entering cell 2, the A.C. signal at microphone 20 will depend on the difference in total electrical and optical energy incident on the cell. By equating, or otherwise relating, the power of each, no A.C. signal will be present at microphone 20. The prior art teaches numerous methods and devices for equating the power generated from two independent sources— for example, varying pulse amplitude, pulsewidth, and the like. The squarewave generator 22 as well may be replaced by a sinewave or other pulse generator or current source, the only limitations being that the output be readily measurable in energy units and provide energy to heat the black sample 14.

Radiometer

Figure 2:
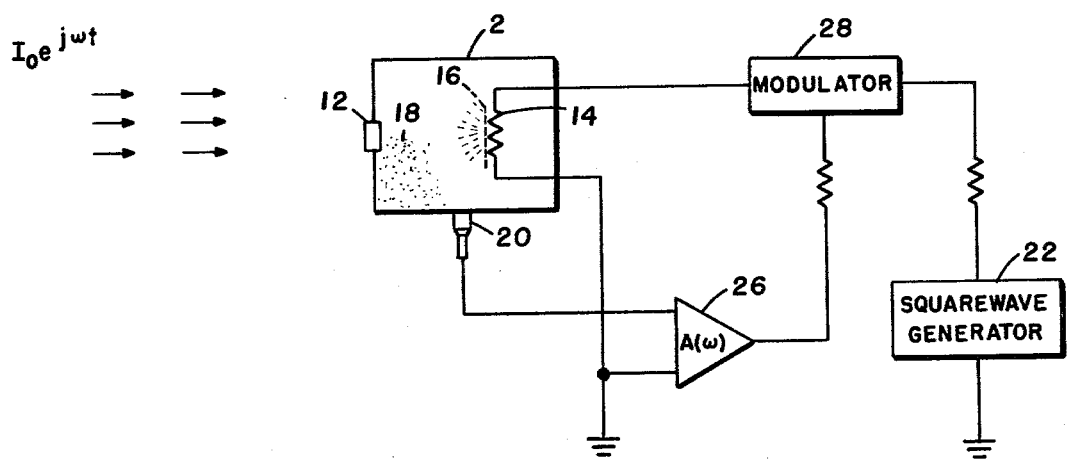
FIG. 2 shows a radiometer feedback path employed to provide a null in the effects generated by heating a black sample optically and electrically.

A radiometer is an instrument which measures the intensity of light. By referring to FIG. 2 it can be seen how the present invention of FIG. 1 can be used in a radiometer application. Light whose intensity is defined generally as $I_0 e^{j\omega t}$ enters window 12 and strikes black sample 14 represented as a resistance in series with squarewave generator 22. If the pressure waves due to light and energy pulses are unequal, the output of microphone 20 will have an A.C. component. By including a lock-in amplifier 24 (see FIG. 1) which is clocked by the modulation source 10 (see FIG. 1), it is readily determined whether the power from squarewave generator 22 must be increased or diminished to effect nullification. An amplifier 26, which receives the A.C. component, or "error signal," from microphone 20 as input, is tuned to angular modulation frequency $\omega$. In feedback fashion shown in FIG. 2, the signal from amplifier 26 enters a modulator 28 to vary the current fed into black sample 14 from squarewave generator 22 until there is no "error signal," i.e. the A.C. component will vanish. When the "error signal" is reduced to zero, either the light source 4 or the squarewave generator 22 (or other measurable heat providing means) may be shut off to yield a peak current, $S_{PAS}$, which is a measure of the energy applied to the black sample 14 by either the light source 4 or the squarewave generator 22 alone. By varying the light source 4 and zeroing the "error signal" by varying the input of the measurable squarewave generator 22, a relationship between heat energy introduced by the squarewave generator 22 and heat energy introduced by the light source 4 can be established using the peak current signal $S_{PAS}$ as an equality factor. In other words, $S_{PAS}$, which represents the peak signal at microphone 22 is equal for each input source (4 or 22) when the heat or longitudinal pressure waves generated by each source is equal. By measuring the energy introduced by the squarewave generator 22 for a given $S_{PAS}$ (where the "error signal" is zero), a corresponding value for energy absorbed due to the light source 4 can be determined. With the black sample 14, all light is absorbed, so the electrical energy measured from the squarewave generator 22 for a given $S_{PAS}$ indicates not only the energy absorption of the black sample 14 but also provides a measurement of the light intensity generated by the light source 4. It should be noted that the peak current signal $S_{PAS}$ for a light input can be generally defined as:

$$S_{PAS} = P_L \cdot K(\lambda) \cdot D_{cell}$$

where $P_L$ corresponds to light intensity; $K(\lambda)$ is generally a wavelength-dependent function which accounts for the optical absorption and heat generation factors of a sample; and $D_{cell}$ refers to cell dependent characteristics such as geometry, location of sample in the cell, and window size. With the black sample 14, $K(\lambda) = 1$ regardless of wavelength. Because the same photoacoustic cell 2 is used for each measurement, the cell dependent variations $D_{cell}$ are eliminated. $S_{PAS}$ thus varies (when there is no other energy source input) only as a function of light intensity $P_L$. The peak current $S_{PAS}$ resulting when only the squarewave generator 22 (or other measurable source) is present is also directly related to the measured energy of the squarewave generator 22. The direct relationship between the energy provided to the black sample 14 by the light source 4 and the squarewave generator 22 (or other measurable source) exists only because the K(λ) and $D_{cell}$ factors in the $S_{PAS}$ definition are eliminated from the cell measurements.

With the black sample 14 in the cell, light intensity into the photoacoustic cell 2 is also the light absorbed. Light absorbed can be measured in terms of the energy required by the squarewave generator 22 to produce a zero "error signal". ($S_{PAS}$ due to the light source 4 equals $S_{PAS}$ due to the squarewave generator 22). The photoacoustic cell 2 thereby acts as a radiometer.

Photoacoustic Spectrometer

In addition to determining light intensity, the present invention can determine the amount of light absorbed by a test sample, in terms of absolute energy units, in a spectrometer-type application. Using the apparatus of FIG. 1, for any given cell enclosing a given gas with light entering at selected spectral and pulse frequencies, cell 2 can be calibrated and the absorption of light by the test sample can be quantitatively measured. The spectrometry method using the photothermophone device of the present invention is now detailed.

Figure 3:
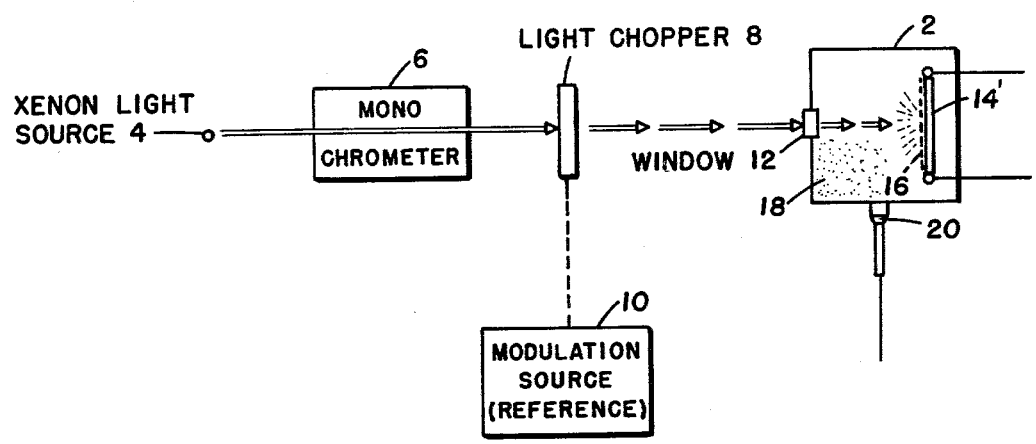
FIG. 3 shows a block diagram of a calibrated PAS wherein a black sample used in the calibrating is replaced by a test sample.

With the black sample 14 in place, the squarewave generator 22 is adjusted to create the A.C. nullification previously described with respect to the radiometer application. Either light source 4 or squarewave generator 22 can then be disconnected. The pressure wave due to or equal to only the Joule-heating results. The power generated by squarewave generator 22, which is proportional to the light absorbed by the black sample 14, is related to the output of microphone 20 after light source 4 or squarewave generator 22 is disconnected. Light source 4 can be reconnected with a change in strength; nullification by adjusting squarewave generator 22 can be effected; the output of microphone 20 can again be related to the power (or current generated by squarewave generator 22; and so on. A functional relationship between the output of microphone 20 and the power generated by squarewave generator 22 (and, hence, the light absorbed by black sample 14) is established. Squarewave generator 22 can then be disconnected and black sample 14 may be replaced by a test sample 14' as shown in FIG. 3. By measuring the output from microphone 20, the light absorbed when light pulses impinge on test sample 14' can be calculated based on the functional relationship established with the black sample 14.

Figure 4:
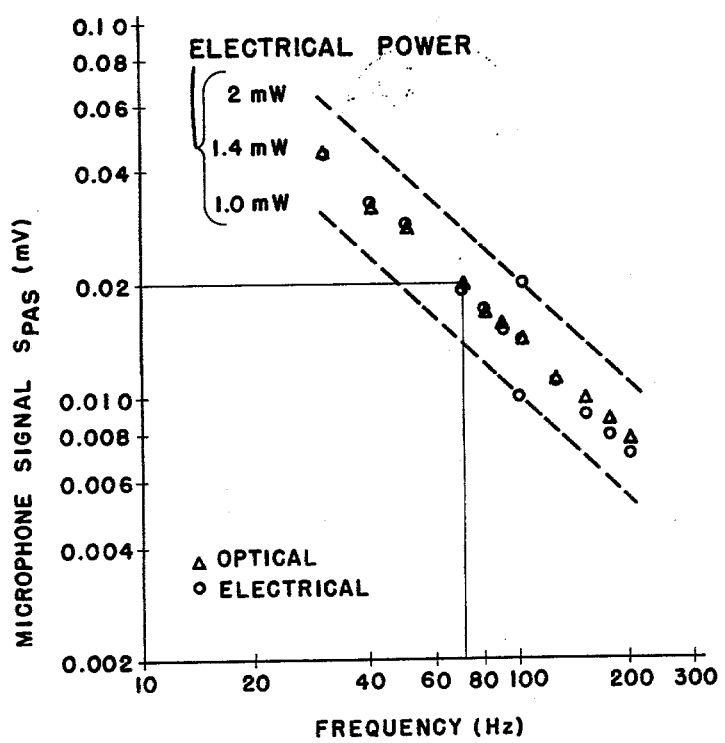
FIG. 4 shows experimental data which illustrate the agreement between the heating effects due optical or light inputs and electrical inputs.

FIG. 4 shows the experimental agreement between the microphone 20 outputs resulting from light absorption and electrical energy conduction, respectively. Changes in microphone 20 output in response to electrical energy power changes at 100 Hz is also illustrated. Finally, with a test sample 14', light absorption can be calculated from FIG. 4. If the output of microphone 20 is measured at 0.02 mv at approximately 70 Hz the electrical power and light intensity can be measured as 1.4 mw.

Given the calibration of light absorption in absolute energy units (based on black sample measurements), various light absorption measurements can be readily made. By varying only the frequency of the pulses of light, an absorption spectrum for the test sample 14' as a function of pulse frequency can be derived (see FIG. 4). By varying only the energy magnitude of the light pulses, the light absorption characteristics as a function of light intensity can be derived by comparing the signals detected at the microphone 22 for the black sample 14 and the test sample 14'. Similarly, once a given magnitude of light from the light source 4 is measured in absolute units taken from the squarewave generator 22 when there is a zero "error signal" with the black sample 14 in the cell 2, the test sample 14' can be placed in the photoacoustic cell 2 instead of the black sample 14 and a measurement of energy absorbed by the test sample 14' as a function of light intensity can be made. Alternatively, cell fluid characteristics can be measured by examining $S_{PAS}$ outputs as a function of various light intensity inputs. Further, by comparing the $S_{PAS}$ light intensity functions for various cell fluids, the relative characteristics of the cell fluids may be determined, keeping in mind that the propogation of light through the cell fluid and the propogation of pressure waves through the cell fluid affect the $S_{PAS}$ output for a given light intensity input.

Various modifications can be made to the invention as specifically described without departing from the invention as contemplated and claimed.

What is claimed is:

1. A self-calibrating photoacoustic spectrometer having a fluid-enclosing cell, said spectrometer comprising:
    means for producing pulses of light;
    means for producing pulses of measurable electrical energy; and
    an insertable solid, metal black, electrically conductive sample placed within the cell, said black sample being heated separately by the incidence of the pulses of light and the pulses of electrical energy onto the black sample.

2. A self-calibrating photoacoustic spectrometer having a fluid-enclosing cell, as in claim 1, further comprising:
    means for directing the pulses of light and the pulses of electrical energy into the cell and to the black sample in order to heat the black sample;
    means for detecting and measuring longitudinal waves generated in the fluid in the cell in response to the heating of the black sample by the light pulses and electrical energy pulses, respectively; and
    means for comparing the magnitude of the longitudinal waves generated by the pulses of light with the magnitude of the longitudinal waves generated by the pulses of energy.

3. A self-calibrating photoacoustic spectrometer having a fluid-enclosing cell, as in claim 2, wherein the light pulse producing means comprises a xenon light source, a monochrometer, and a light chopper; wherein the means for producing electrical energy pulses comprises a squarewave generator; and wherein the means for directing the light pulses and the electrical energy pulses comprises a window in the cell for entering chopped light into the cell directed toward the location of the black sample, and electrical means for connecting the squarewave generator to the black sample and directing the electrical squarewaves into the black sample.

4. A self-calibrating photoacoustic spectrometer having a fluid-enclosing cell, as in claim 3, further comprising:
    means for synchronizing the light chopper with the squarewave generator, wherein the synchronizing means causes the chopped light from the xenon light source and squarewaves from squarewave generator to enter the cell in alternating fashion.

5. A self-calibrating photoacoustic spectrometer having a fluid-enclosing cell, as in claim 4, further comprising:
  means for varying the electrical energy pulse input such that the energy of the longitudinal waves detected due to the electrical energy pulse input is equal to that of the longitudinal waves due to the light pulse input.

6. A self-calibrating photoacoustic spectrometer having a fluid-enclosing cell, as in claim 5, further comprising:
  a test sample;
  means for replacing the black sample with the test sample; and
  means for continuing the light pulses directed toward the test sample in the cell and discontinuing the electrical energy pulses.

7. A self-calibrating photoacoustic spectrometer having a fluid-enclosing cell, as in claim 6, further comprising:
  means for measuring the energy of the longitudinal wave generated due to the heating of the test sample by the light pulses, and
  means for determining the measured energy in absolute units, with the black sample in the cell, of a longitudinal wave having the same energy as the longitudinal wave generated due to the test sample by the light pulses.

8. A radiometer for measuring, in absolute quantitative energy units, the intensity of light entering a photoacoustic cell, comprising:
  a solid black, electrically conductive sample placed within the cell;
  a source of light directed into the cell and absorbed by the black sample;
  a source of measurable electrical energy fed to the sample in the cell; and
  means for comparing the amount of energy emanating from the black sample due to the light absorbed by the black sample with the amount of energy emanating from the black sample due to the measurable electrical energy fed to the black sample.

9. A combination photothermophone comprising:
  a self-calibrating fluid-filled cell which is both a photoacoustic cell having a pulsating light input and a thermophone cell having a pulsating electrical input, said self-calibrating cell comprising:
  a sample which absorbs the pulses of light, converts the light into heat energy which causes the fluid in the cell to expand and contract, and produces longitudinal waves as a result of the expansion and contraction; and which conducts the current emanating from the electrical input, Joule-heats in response to the passing of the current which causes the fluid in the cell to expand and contract, and produces longitudinal waves as a result of the expansion and contraction.

10. A method for calibrating an operating photoacoustic fluid-enclosing cell comprising the steps of:
  periodically generating light pulses at a pulse frequency;
  generating measurable energy pulses at the same pulse frequency as that of the light pulses;
  directing the generated light pulses and the generated energy pulses into the cell to a black sample thereby heating the black sample; and
  comparing the heating effects of the black sample resulting from the light pulses with the heating effects resulting from the energy pulses, respectively.

11. A method for calibrating an operating photoacoustic fluid-enclosing cell, as in claim 10, further comprising the step of:
  alternating the generating of the light pulses and the energy pulses.

12. A method for calibrating an operating photoacoustic fluid-enclosing cell, as in claim 10, further comprising the step of:
  generating an error output signal corresponding to the difference in the magnitudes of the heating effects caused independently by the light pulses and the energy pulses, respectively.

13. A method for calibrating an operating photoacoustic fluid-enclosing cell, as in claim 12, further comprising the steps of:
  adjusting the magnitude of the measurable energy pulses such that the magnitude of the error output signal generated is zero, indicating that there is an equality in the heating effects from the light pulses and energy pulses, respectively; and
  measuring the energy value of the measurable energy pulses required to produce a zero error output signal.

14. A method for calibrating an operating photoacoustic fluid-enclosing cell, as in claim 13, further comprising the steps of:
  discontinuing either the light pulses or the energy pulses when the error output signal is zero and after the energy value of the measurable energy pulses is measured;
  measuring the value of a remnant output signal corresponding to the magnitude of the heating effect with either the light or energy pulse input discontinued; and
  correlating the value of the measurable energy pulses with a corresponding measured remnant output signal.

15. A method for calibrating an operating photoacoustic fluid-enclosing cell, as in claim 14, further comprising the step of:
  defining a relationship between the value of the remnant output signal and the value of the measured energy pulses.

16. A method for calibrating an operating photoacoustic fluid-enclosing cell, as in claim 15, further comprising the steps of:
  replacing the black sample with a test sample;
  directing light pulses onto the test sample, thereby heating the test sample; and
  generating a second output signal corresponding to the heating effects caused by the directed light pulses.

17. A method for calibrating an operating photoacoustic fluid-enclosing cell, as in claim 16, further comprising the step of:
  determining the value of measured energy pulses which would be required to produce a remnant output signal that would be the same as the second output signal, based on the defined relationship.

18. A method for calibrating an operating photoacoustic fluid-enclosing cell, as in claim 17, further comprising the step of:

associating the determined value of energy pulses required to produce the second output signal with the absorption of light by the test sample.

19. A method for calibrating an operating photoacoustic fluid-enclosing cell, as in claim 10, wherein the comparing of heating effects comprises the steps of:
   detecting and measuring longitudinal waves resulting from the expansion and contraction of the fluid in the cell as the black sample heats; and
   comparing the detected and measured longitudinal waves due to the light pulses with the longitudinal waves due to the energy pulses.

20. A method for calibrating an operating photoacoustic fluid-enclosing cell, as in claim 19, further comprising the step of:
   adjusting the measurable energy pulses to equate the longitudinal waves resulting from the light pulses with the longitudinal waves resulting from the energy pulses.

21. A method for calibrating an operating photoacoustic fluid-enclosing cell, as in claim 19, further comprising the steps of:
   transducing the longitudinal waves into electrical signals;
   comparing the electrical signals corresponding to the longitudinal waves resulting from the light pulses with the electrical signals corresponding to the longitudinal waves resulting from the energy pulses; and
   adjusting the measurable energy pulses such that the electrical signals resulting from the measurable energy pulses are equal to the electrical signals resulting from the light pulses.

22. A method for calibrating an operating photoacoustic fluid-enclosing cell, as in claim 21, further comprising the steps of:
   measuring the value of the measurable energy pulses when the electrical signals resulting from the light pulses equal the electrical signals resulting from the measurable energy pulses;
   discontinuing either the light pulses or the measurable energy pulses after the value of the measurable energy pulses is measured;
   measuring a transduced electrical remnant signal after the light pulses or measurable energy pulses are discontinued; and
   defining a relationship between the measured value of the measurable energy pulses and the transduced electrical remnant signal.

23. A method for calibrating an operating photoacoustic fluid-enclosing cell, as in claim 22, wherein calibration is used in determining characteristics of a test sample, further comprising the steps of:
   replacing the black sample with the test sample;
   directing light pulses onto the test sample thereby heating the test sample and generating longitudinal disturbances;
   transducing the longitudinal disturbances into electrical signals; and
   measuring the electrical signals.

24. A method for calibrating an operating photoacoustic fluid-enclosing cell, as in claim 23, wherein the calibration is used in determining characteristics of a test sample, further comprising the step of:
   determining the value of measurable energy pulses which would be required to produce a transduced electrical remnant signal equal to electrical signals, based on the defined relationship.

25. The method for calibrating an operating photoacoustic fluid-enclosing cell, as in claim 10, wherein the comparing of heating effects comprises the step of:
   detecting and measuring longitudinal waves in the cell resulting from the expansion and contraction of the fluid in the cell as the black sample absorbs heat due to the inputting of the light pulses and the energy pulses.

26. A method for calibrating an operating photoacoustic fluid-enclosing cell, as in claim 25, further comprising the step of:
   adjusting the pulses from the energy source such that the heating effects resulting from the directing of energy pulses into the black sample are equal to the heating effects due to the absorption of light pulses by the black sample.

27. A method for determining the optical absorption characteristic of a test sample, comprising the steps of:
   placing a black sample in the cell;
   directing optical energy and measurable energy from respective sources to be absorbed as heat by the black sample;
   maintaining the quantity of optical energy constant and varying the quantity of the measurable energy to generate equal pressure effects in the cell emanating from the black sample due to the two energy sources; and
   measuring, in absolute energy units the quantity of the measurable energy required to effect the equal pressure effects.

28. A method, as in claim 27, further comprising the steps of:
   measuring the heating effect due to only the measurable energy for a specific quantity of the measurable energy and defining a relationship between the quantity of measurable energy and the heating effects resulting therefrom;
   replacing the black sample with the test sample after the relationship is defined; and
   measuring the heating effect due to only optical energy absorption with the test sample in the cell.

29. A method, as in claim 28, further comprising the step of:
   indicating the quantity of measurable energy that would be required, in accordance with the defined relationship, to produce a heating effect equal to the heating effect due to only optical absorption with the test sample in the cell.

30. A method, as in claim 28, further comprising the step of:
   comparing the heating effect due to only optical energy absorption produced with the test sample in the cell with the heating effect due to only optical energy absorption produced with the black sample in the cell.

31. A method, as in claim 28, further comprising the steps of:
   resetting the constant quantity of optical energy maintained thereby providing a different pressure effect due to only optical absorption; and
   indicating, in absolute energy units, the quantity of the measurable energy with the black sample in the cell that would be required to produce a pressure effect equal to the new pressure effect for each reset constant quantity of optical energy.

32. A method, as in claim 31, further comprising the step of:

defining an optical absorption function for the test sample comprising the step of:
associating each constant quantity of optical energy with the quantity of measurable energy required to produce the equal pressure effect.

33. A method, as in claim 27, further comprising the steps of:
resetting the constant quantity of optical energy maintained, thereby providing a different pressure effect due to only optical absorption; and
indicating, in absolute energy units, the quantity of the measurable energy with the black sample in the cell that would be required to produce a pressure effect equal to the new pressure effect for each reset constant quantity of optical energy.

* * * * *